United States Patent [19]

Rubin et al.

[11] 3,969,322

[45] July 13, 1976

[54] NOVEL PROCESS AND PRODUCT

[75] Inventors: Isaac D. Rubin, Wappingers Falls; Richard F. Love, Fishkill; Charles B. Holder, Wappingers Falls, all of N.Y.

[73] Assignee: Texaco Inc., New York, N.Y.

[22] Filed: Dec. 2, 1974

[21] Appl. No.: 528,980

Related U.S. Application Data

[62] Division of Ser. No. 382,102, July 23, 1973, Pat. No. 3,890,357.

[52] U.S. Cl. .................. 260/63 N; 252/51.5 A; 260/65; 260/878 R; 260/897 B; 526/19.49
[51] Int. Cl.² .................. C08G 6/00; C08F 216/36
[58] Field of Search .............. 260/63 N, 65, 878 R, 260/897 B, 80.7, 80.78

[56] References Cited

UNITED STATES PATENTS

| | | | |
|---|---|---|---|
| 2,769,783 | 11/1956 | Hollyday | 260/65 X |
| 2,933,480 | 4/1960 | Gresham et al. | 260/80.78 X |
| 3,383,373 | 5/1968 | Waples | 260/897 B X |
| 3,395,198 | 7/1968 | Taniguchi et al. | 260/897 B |
| 3,681,302 | 8/1972 | Sweeney | 260/80.78 |
| 3,736,304 | 5/1973 | Masson et al. | 260/65 X |
| 3,751,522 | 8/1973 | Lachowicz et al. | 260/80.78 X |
| 3,751,523 | 8/1973 | Lachowicz et al. | 260/80.78 X |

*Primary Examiner*—Lucille M. Phynes
*Attorney, Agent, or Firm*—T. H. Whaley; C. G. Ries; Carl G. Seutter

[57] ABSTRACT

Amino ester products, useful as additives to lubricating oils, may be prepared by reaction of an alpha-nitroketone and a tertiary aminoalcohol.

17 Claims, No Drawings

NOVEL PROCESS AND PRODUCT

This is a division of application Ser. No. 382,102, filed July 23, 1973, now U.S. Pat. No. 3,890,357 granted June 17, 1975.

FIELD OF THE INVENTION

This invention relates to a novel process for preparing polymeric aminoesters. More particularly this invention relates to polymeric aminoesters which may find use as additives to petroleum oils including lubricating oils.

BACKGROUND OF THE INVENTION

Alpha-nitroketones may be converted into a wide variety of derivative products including the carbonyl-containing moiety of the alpha-nitroketone. However prior processes for derivatizing and cleaving alpha-nitroketones utilize undesirable conditions resulting inter alia from the presence of vigorous catalyst (typically strong bases). Even with these conditions however, it has not heretofore been possible to utilize the practices of the prior art to satisfactorily produce aminoesters from alpha-nitroketones under commercial conditions.

It is an object of this invention to provide a process for the preparation of aminoesters. It is another object of this invention to provide aminoester products which may find use as additives to petroleum oils typified by lubricating oils. Other objects will be apparent to those skilled in the art from inspection of the following description.

In accordance with certain of its aspects, the novel method of this invention may comprise reacting (i) a nitroketonized polymer bearing pendant alpha nitroketone groups with (ii) a tertiary amino alcohol thereby forming a polymer bearing pendent aminoester groups; and recovering said polymer bearing said pendant aminoester groups.

In accordance with certain of its more specific aspects, the method of this invention for preparing an aminoester

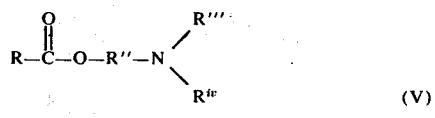

may comprise reacting an alpha-nitroketone

with a tertiary amino alcohol

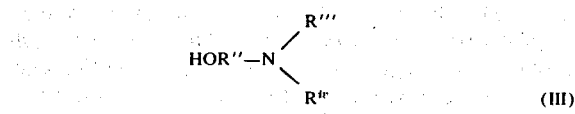

wherein R, R''', and $R^{iv}$ are saturated hydrocarbon, R' is hydrogen or saturated hydrocarbon, and R'' is divalent saturated hydrocarbon thereby forming product aminoester; and recovering said aminoester.

DESCRIPTION OF THE INVENTION

The alpha-nitroketones which may be employed in practice of the process of this invention may be compounds primarily characterized by the presence of a nitro- group and an alpha-keto-group bonded to a hydrocarbon nucleus. The hydrocarbon nucleus may be typically derived from inert alkyl, aryl, alkaryl, aralkyl, or cycloalkyl moieties. In one embodiment of the process of this invention, the hydrocarbon nucleus of the charge alpha-nitroketone may be monomeric in nature. In another embodiment of the process of this invention, the nucleus of the charge alpha-nitroketone may be polymeric in nature. In this latter embodiment, the hydrocarbon nucleus of the charge alpha-nitroketone may be in a long polymeric chain, containing residual unsaturation, typified for example by EPT polymers (i.e. copolymers of ethylene, propylene, and a third monomer such as 1,4-hexadiene, etc.)

The charge alpha-nitroketone is characterized by presence of non-terminal carbonyl (—CO—) and by the nitro(—NO$_2$) group. In the charge alpha-nitroketone, the nitrogroup is on a carbon atom immediately adjacent to a carbonyl group.

The charge alpha-nitroketone may preferably have the formula

In the above compound, R and R' may each independently be a monovalent saturated hydrocarbon radical selected from the group consisting of alkyl, aralkyl, cycloalkyl, aryl, and alkaryl including such radicals when inertly substituted. R' may alternatively be hydrogen. When R or R' is alkyl, it may typically be methyl, ethyl, n-propyl, isopropyl, n-butyl, i-butyl, sec-butyl, amyl, octyl, decyl, octadecyl, etc. When R or R' is aralkyl, it may typically be benzyl, beta-phenylethyl, etc. When R or R' is cycloalkyl, it may typically be cyclohexyl, cycloheptyl, cyclooctyl, 2-methylcycloheptyl, 3-butylcyclohexyl, 3-methylcyclohexyl, etc. When R or R' is aryl, it may typically be phenyl, naphthyl, etc. When R or R' is alkaryl, it may typically be tolyl, xylyl, etc. R or R' may be inertly substituted; i.e. it may bear a non-reactive substituent such as alkyl, aryl, cycloalkyl, ether, etc. Typically inertly substituted R or R' groups may include 2-ethoxyethyl, 4-methyl cyclohexyl, p-chlorophenyl, 3-chloro-5-methylphenyl, etc. The preferred R or R' groups may be lower alkyl, i.e. $C_1$–$C_{30}$ alkyl, groups including eg methyl, ethyl, n-propyl, i-propyl, butyls, amyls, hexyls, octyls, decyls, etc. R may preferably be hexyl or octyl. Preferably R may be octyl and R' may be hydrogen. R and R' may together form a cyclic moiety such as cyclohexyl, cyclooctyl, cyclododecyl, etc.

A preferred charge alpha-nitroketone may be

Typical of the charge monomer-type nitroketones which may be used in practice of the process of this invention may be those set forth in the following table:

TABLE I 1-nitro-2-butanone
3-nitro-2-butanone
2-nitro-3-pentanone
1-nitro-2-pentanone
3-nitro-2-pentanone
1-nitro-2-hexanone
3-nitro-2-hexanone
4-nitro-3-hexanone
1-nitro-2-heptanone
3-nitro-4-heptanone
5-nitro-4-octanone
4-nitro-5-decanone
5-nitro-4-dodecanone
1-nitro-1-phenyl-propanone-2
1-nitro-2-cyclohexanone
1-nitro-2-cyclooctanone
1-nitro-2-cyclododecanone
1-nitro-2-octanone
1-nitro-2-decanone
2-nitropropiophenone
alpha-nitrobenzyl-phenyl-ketone
1-4-diphenyl-3-nitro-2-butanone
3-nitro-4-pentadecanone
1-nitro-2-hexadecanone
9-nitro-8-heptadecanone
8-nitro-9-heptadecanone
1-nitro-2-octadecanone
1-nitro-2-heneicosanone The preferred charge nitroketone may be 1-nitro-2-octanone or 1-nitro-2-decanone.

It is a particular feature of this invention that the charge alpha-nitroketone may be a nitroketonized polymer wherein the nitroketone moiety may be pendant on a polymeric chain. Typical of these charge materials, which when nitrokentonized are useable in te instant process, may be polymers, (containing residual unsaturation, including residual terminal unsaturation) wherein R is a polymer moiety containing a carbon-to-carbon backbone, possessing residual unsaturation, typified by ethylene-propylene-third monomer. Typical of these base polymer molecules which, when nitroketonized, may be used as charge materials to the process of this invention may be the following:

a. EPT terpolymer prepared from ethylene, propylene, and 1,4-hexadiene and having a molecular weight $\overline{M}_n$ of 300–100,000, preferably 20,000–70,000, say 68,000 as typified by the commercially available product marketed by DuPont under the trademark Nordel 1320;

b. 1,2-polybutadiene, prepared by polymerizing butadiene-1,3 in the presence of 15 wt % butyl lithium in hexane or tetrahydrofuran at 0°–60°C, having a molecular weight $\overline{M}_n$ of 3,000–20,000;

c. polypropylene having a molecular weight $\overline{M}_n$ of 500–3500, typically 650–2600, say 500–995;

d. polybutylene having a molecular weight $\overline{M}_n$ of 300–1900, typically 1100;

e. a copolymer of ethylene and butylene having a molecular weight $\overline{M}_n$ of 810;

f. an EPT terpolymer having a molecular weight $\overline{M}_n$ of 3000–30,000, typically 3970–6950, prepared by copolymerizing ethylene, propylene, and 1,4-hexadiene at 0°–20°C in the presence of tri-n-butyl vanadate catalyst and diethyl aluminum chloride cocatalyst in n-heptane solvent in the presence of hydrogen. A typical such polymer contains 32 mole % propylene, 2.8 mole % 1,4-hexadiene, and 65.2 mole % ethylene, and has one double bond for each 1000–2000, say 1160–1880 molecular weight units.

These polymers, which may be nitroketonized contain residual unsaturation (typically in amount equivalent to one double bond for each 300–10,000 molecular weight units) of the type RCH=CH₂ or RCH=CHR preferably mainly on side chains so that rupture of the polymer backbone chain does not occur on cleavage of the nitroketone to aminoester. Nitroketonization of such polymers, as is well-known, occurs typically by reaction of the olefin (e.g. the double bonds of the polymer side chain), with $N_2O_4$ and oxygen to give a nitro peroxynitrate which, upon reaction with e.g. dimethylformamide, is converted to the corresponding nitroketone.

In the preferred embodiment, each of the compounds containing the base group R (whether monomeric or polymeric in nature) may contain one nitro group per ketone group. When the R group is a monomeric group, typically containing less than 30 and commonly containing 5–25 carbon atoms, preferably there may be one nitroketone unit per molecule (i.e. one nitro function and one ketone function).

When the R moiety in the charge nitroketone is derived from a polymer, the polymer molecule may contain a wide range of nitroketone groups per mole molecule, depending upon the number of double bonds in the parent polymer and the degree of nitroketonization. Where the aminoester to be prepared is to be oil soluble, as in the preferred embodiment, the number of nitroketone groups may preferably be one for each 300–10,000 molecular weight units, preferably one for each 1000–5000 molecular weight units, say one for each 1800 molecular weight units. Preferably in this instance, the greatest solubility in lube oil systems may be achieved when the molecular weight $\overline{M}_n$ is 300–15,000 (of the charge polymer).

The preferred polymer-derived R group may be that derived from the terpolymer of ethylene-propylene - 1,4-hexadiene, which when nitroketonized may contain the following repeating groups in the polymer chain:

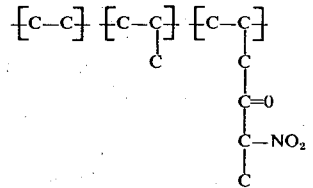

Typical of the nitroketonized polymers which may be employed as charge to the process of this invention is that prepared by reacting 1,2-polybutadiene ($\overline{M}_n$ of 5000–10,000) with dinitrogen tetroxide and oxygen in toluene. After reaction at 0°C for 115 minutes, $N_2O_4$ had been added in amount sufficient to react with 8% of the available double bonds. After purging with oxygen, the nitro peroxynitrate is reacted with dimethylformamide at minus 10°C for 15 minutes and the reaction mixture is worked up to yield product nitroketonized 1,2-polybutadiene.

In the preferred practice of the process of this invention, the preferred monomeric-type charge alphanitroketone may be 1-nitro-2-octanone or 1-nitro-2-decanone; and the preferred polymer-type charge nitroketone may be nitroketonized ethylene-propylene-1,4-hexadiene.

In practice of the process of this invention, the charge tertiary amino alcohol may correspond to the following formula:

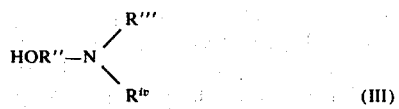
(III)

wherein R''' and R$^{iv}$ may be saturated hydrocarbons; and R'' may be a divalent saturated hydrocarbon function. It will be apparent to those skilled in the art that the R, R', R''', and R$^{iv}$ groups in any given formula need not be the same group, although they may be. The divalent R'' group may be derived from the same group as R, but it need not be, e.g. R may be methyl and R'' may be ethylene. It will be apparent that R''' and R$^{iv}$ may be cyclicized to form eg a piperidine ring, a pyrrolidine ring, etc.

In the preferred embodiment, the compound III may be one wherein the R'', R''', and R$^{iv}$ groups are derived from lower alkyl and contain 1–10, say 1–5 carbon atoms; and illustrative alcohols which may be employed may include the following:

TABLE II

Dimethylaminoethanol
1-Dimethylamino-2-propanol
2-Dimethylamino-1-butanol
3-Dimethylamino-1-propanol
Diethylaminoethanol
2-Di-n-propylamino-1-hexanol
Dioctylaminoethanol
2-Dioctylamino-1-hexanol
2-Dinonylamino-1-butanol
2-Dibutylamino-1-decanol
Dibutylaminoethanol
1-Diethylamino-2-propanol
3-Dibutylamino-1-propanol
3-Diethylamino-1-propanol The preferred aminoalcohols may be dimethylamino alcohols preferably dimethylamino ethanol.

In practice of the process of this invention, the nitroketone and the tertiary amino alcohol may be added to the reaction mixture in mole ratio (of tertiary amino alcohol to nitroketone charge) of 1–100:1, preferably 1–15:1, say about 1:1 when the nitroketone is a monomer and a mole ratio of 1–100:1 preferably 5–15:1, say about 9:1 when the nitroketone is a polymer.

It is a feature of the process of this invention that it may, if desired, be carried out in the presence of 0–100, preferably 1–50, say 10 parts (per part of total reactants) of an inert diluent, in which the reactants are preferably soluble, typified by a hydrocarbon such as n-hexane, n-heptane, xylene, ethylbenzene, toluene, etc.; halogenated hydrocarbons typified by dichlorobenzene; tertiary alcohols including tertiary butyl alcohol; ethers typified by dioxane, tetrahydrofuran, etc.

In the preferred embodiment of this invention, however, the reaction may be carried out in the presence of an excess of tertiary amino alcohol, preferably that being employed as reactant.

Preferably reaction may be carried out at temperature of 50°–200°C, typically 60°–130°C, say 80°C at a pressure of 0–200 psig typically 0–50 psig, say 0 psig for a period of time of 1–50 hours, preferably 3–30 hours, say 4 hours for "monomeric reactions" and 24 hours for "polymeric reactions". It is a particular feature of the process of this invention that moderate temperatures eg 70°–100°C may be employed.

Although it may be possible to carry out the process of this invention in the presence of catalyst, it is a particularly desirable feature that the process proceeds readily in the absence of added catalyst. It appears that the reaction may be autocatalytically influenced by the tertiary amino alcohol reactant.

When the reaction is carried out in the presence of catalyst, catalytic amounts, i.e. 0 to 5 parts, preferably 1 to 2 parts, say 1.5 parts of catalyst per 100 parts of nitroketone may be present in the reaction medium. The catalyst may typically be a basic catalyst. When the reaction is carried out in the presence of basic catalyst, it may be desirable to use oxides, hydroxides, or alkoxides of alkali metals or alkaline earth metals. Typical of such basic catalysts may be sodium methoxide or metal soaps RCOOM. It may be possible to use organic amines as base catalysts, typically tertiary organic amines such as triethylamine or tetramethylguanidine.

In accordance with another aspect of this invention, it may be possible to use, as catalyst for the process of this invention, salts (of eg alkali metals such as potassium or sodium or of alkaline earth metals such as calcium) of fatty acids, or carbonates, fluorides, or of weakly acidic ion exchange resins. Typical of these latter may be Amberlite IRC-50 (sodium salt).

In the preferred embodiment, the reaction may be auto-catalyzed by the tertiary amino alcohol reactant; and no additional catalyst may normally be employed.

During the course of the reaction, the alphanitroketone and the tertiary amino alcohol react to form the product aminoester and, as by-product, a nitrohydrocarbon typically having the following formula:

(V)

The reaction which occurs may typically be as follows:

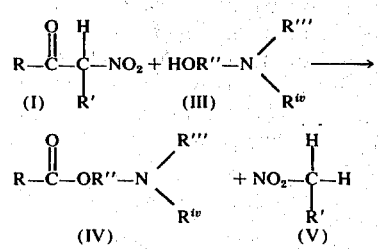

Typically the reaction may be carried out under reflux (at reflux temperature) in the presence of diluent-solvent, typically benzene, which may be distilled from the reaction mixture. Upon condensation of the distillate, it may be found that the distillate contains (per mole of charge nitroketone) 0.25–1 moles preferably 0.4–0.8 moles, say 0.75 moles of by-product nitro compound, typically nitromethane or nitroethane.

The monomer-derived residue may then be distilled, typically at reduced pressure of 1–50 mm. Hg to yield (per mole of charge nitroketone) 0.2–1 moles, preferably 0.4–0.8 moles, say 0.75 moles of desired product aminoester. Typically desired product may be obtained in yields of 20–100%, preferably 40–80%, say 75%.

When the charge nitroketone includes a polymer-type moiety typified by the EPT polymer prepared from ethylenepropylene-1,4-hexadiene, the polymer product may be obtained by water washing to remove excess amino alcohol and then distilling off remaining diluent-solvent (typically benzene).

Preferably the reaction may be carried out under substantially anhydrous conditions, i.e. containing less than 1%, and more preferably less than 0.1% water.

The amino ester products which may be prepared by the process of this invention may typically have the following formula:

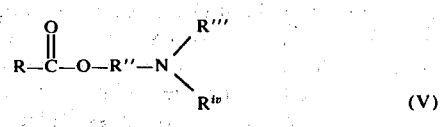
(V)

wherein R, R''', and R$^{iv}$ may be saturated hydrocarbon as noted supra, and R'' may be a divalent saturated hydrocarbon as noted supra.

Typically the non-polymeric aminoester monomer prepared by the process of this invention may be moderate-to-high boiling, clear-to-pale-yellow liquids. Product polymers may be viscous, tacky, or rubbery.

Typical of the monomer-type products which may be prepared by the process of this invention may be those set forth in the following Table III.

TABLE III

N,N-dimethylaminoethyl heptanoate
N,N-dimethylaminoethyl nonanoate
N,N-diethylaminoethyl butanoate
N,N-diethylaminoethyl propionate
N,N-di-n-butylaminoethyl butanoate
N,N-di-n-butylaminoethyl pentanoate
N,N-dimethylamino-n-propyl hexanoate
N,N-dimethylaminoethyl hexanoate
N,N-di-n-propylaminoethyl butanoate
N,N-dioctylaminohexyl propionate
N,N-dimethylaminoethyl propionate
N,N-dipropylaminoethyl propionate
N,N-dimethylaminoethyl stearate
N,N-dimethylaminoethyl myristate In the case of the polymer product aminoester derived from eg the terpolymer of ethylene-propylene-1,4-hexadiene, the composition may typically contain the following repeating groups:

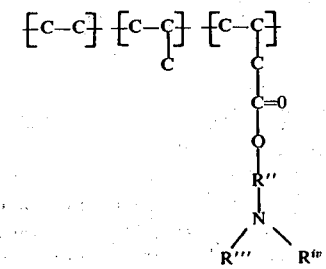

Such a composition may contain 40 mol %—80 mole % derived from ethylene, 20 mol %—60 mol % derived from propylene, and 0.1 mol %—5 mol % derived from third monomer.

In a specific instance for example the formula may be

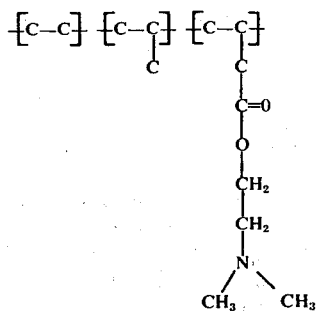

The novel aminoester polymer products may include those having a carbon-carbon (i.e. a carbon-containing) backbone chain and pendant therefrom (typically through an alkylene eg —CH$_2$— linkage) a plurality of groups

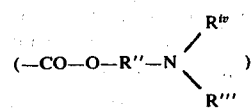

wherein R''' and R$^{iv}$ are monovalent saturated hydrocarbon and R'' is divalent saturated hydrocarbon, said polymer typically having a molecular weight $\overline{M}_n$ of 300–50,000, preferably 800–15,000, say 5000, and 1

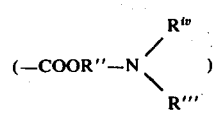

group per 300–10,000, preferably 1000–5000, say 1800 molecular weight units in said molecule. The preferred of said groups are the carbo-N,N-di (lower alkyl) amino alkoxy groups.

Typical of other specific polymer products which may be prepared by the process of this invention are those set forth in the following table:

TABLE IV a. Dimethylaminoethyl ester of a completely nitroketonized EPT - specifically the nitroketonized terpolymer of ethylene-propylene-1,4-hexadiene containing 65.2 mol % ethylene, 32 mole % propylene, and 2.8 mole % hexadiene, $\overline{M}_n$ of 4445 and containing 1 nitroketone group per 1220 molecular weight units;

b. 3-dibutylaminopropyl ester of a completely nitroketonized EPT - specifically the nitroketonized terpolymer of ethylene-propylene-1,4-hexadiene containing 65.2 mol % ethylene, 32 mole % propylene, and 2.8 mole % hexadiene, $\overline{M}_n$ of 4445 and containing 1 nitroketone group per 1220 molecular weight units;

c. Diethylaminoethyl ester of a completely nitroketonized EPT - specifically the nitroketonized terpolymer of ethylene-propylene-1,4-hexadiene containing 65.2 mole % ethylene, 32 mole % propylene, and 2.8 mole % hexadiene, $\overline{M}_n$ of 4445 and containing 1 nitroketone group per 1220 molecular weight units;

d. Dimethylaminoethyl ester of a 2% (of the available unsaturation) nitroketonized 1,2-polybutadiene $\overline{M}_n$ of 6150;

e. 3-Dibutylaminopropyl ester of a 2% (of the available unsaturation) nitroketonized 1,2-polybutadiene $\overline{M}_n$ of 6150;

f. Dimethylaminoethyl ester of an 8% (of the available unsaturation) nitroketonized 1,2-polybutadiene $\overline{M}_n$ of 6150;

g. 3-Dibutylaminopropyl ester of an 8% (of the available unsaturation) nitroketonized 1,2-polybutadiene $\overline{M}_n$ of 6150;

It is a particular feature of the products of this invention that they may find use (i) as additives to impart good dispersancy to motor oils including lubricating oils; (ii) as additives to impart good dispersancy in fuel oils; (iii) when quaternized, as fat softeners, detergents, etc. Products wherein R is polymeric are particularly suitable for the first of these uses. When R is "monomer-derived", the products may find particular use in the second and third areas. The polymer derived products may be useful as additives to improve the viscosity index of lubricating oils.

These novel products may find particular use as additives to lubricating oils, petroleum base or synthetic (eg ester type such as polyester oils); it may be found that by presence of these novel compounds, the dispersancy of such oils may be substantially improved.

Commonly these products may be useful in the form of concentrates containing 10–70 parts, preferably 20–60 parts, say 50 parts of aminoester per 30–90 parts, preferably 20–80 parts, say 50 parts of inert diluent-solvent. Inert diluent-solvents may include hydrocarbons such as toluene, and more preferably oils including lubricating oils — synthetic or petroleum based. A typical concentrate may include 35 parts of the dimethylaminoethyl derivative of the nitroketonized polymer prepared from ethylene-propylene-1,4-hexadiene in 65 parts of 100 E Pale Stock HF (a paraffinic distillate oil 39 SUS viscosity at 210°F.) lubricating oil.

The dispersancy of a lubricating oil may be determined by a standard Bench Sludge Test. In this test, the oil to be tested (containing 1.5–3% of additive) is introduced into a test bottle together with a suspension of 6 wt % of titanium dioxide in oil. The mixture is heated at elevated temperature for an extended period of time with agitation; a measured sample is then centrifuged and the depth of the sediment is recorded in millimeters. The scale may cover a range of 0–100; and commonly these readings may be less than 10. A reading of 0.8 or less is considered sufficiently good on this BSI test so that the sample may be subjected to the more severe BSII test.

In the BSII test, an aliquot sample is mixed with a standard hydrocarbon engine blowby — and thus this test is more correlative with actual conditions of use than is the BSI test. A BSII rating of less than about 1.8 is generally considered to be a significant indication of high dispersancy of the additive.

In accordance with certain of its aspects, a product prepared in accordance with this invention may comprise a dispersing amount of

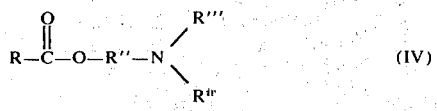

(IV)

wherein R, R''', and R$^{iv}$ are saturated hydrocarbon and R'' is divalent saturated hydrocarbon; in an excess of a lubricating oil.

The base oil, the dispersancy rating of which may be improved by use of the novel additives of this invention, may include petroleum based oils or synthetic ester based oils.

Typical of the petroleum base lubricating oils which may be improved may be those formulated for use in automotive engines.

The dispersing amount of additive which may be used to achieve the unexpected and improved dispersancy may be 0.1–10 parts, preferably 1–4 parts, say 2 parts of additive per 100 parts of lubricating oil. In typical practice of this invention it may be found that addition to these oils of 1–5%, say 2% of a typical aminoester of this invention may desirably decrease the sludging ratings to a satisfactory level. As it is apparent to those skilled in the art, it is unexpected that such small quantities of additives should permit attainment of the outstanding desired decrease in dispersancy.

The novel polymeric compositions of this invention may permit attainment of improvement in viscosity index. Typically there may be obtained an increase of 30 units or more over the VI of the base oil. This may be achieved by use of a viscosity index improving amount eg 0.5–3, say 1.6 parts of polymer additive per 100 parts of lubricating oil composition.

Practice of the process of this invention may be apparent to those skilled in the art from inspection of the following examples wherein, as elsewhere in this specification, all parts are parts per weight unless otherwise stated. In the examples as elsewhere, unfilled valence bonds may be filled with hydrogen atoms.

DESCRIPTION OF SPECIFIC EMBODIMENTS

EXAMPLE I

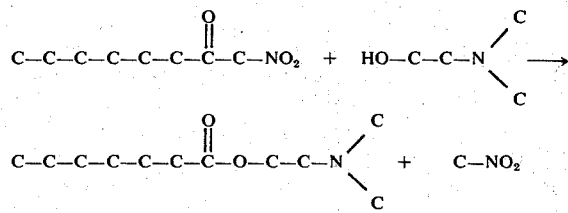

In this example which represents practice of a preferred embodiment of this invention, 8.65 parts of 1-nitro-2-octanone, 4.5 parts of dimethylaminoethanol, and 88 parts of dry benzene are heated in a reaction vessel to reflux over a period of three hours. During this period the nitro compound and the aminoalcohol react to produce aminoester and by-product nitromethane. Distillation permits recovery of 44 parts of benzene containing 1.37 parts (45% yield) of nitromethane. After removal of residual benzene, the residue is then further distilled at reduced pressure of 1–2 mm Hg to yield two fractions: (a) 5.77 parts of N,N-dimethylaminoethyl heptanoate b.p. 92°C/1 mm and (b) a second fraction containing 2.1 parts of heptanoic acid boiling at 94°–102°C/2mm. Yield of the desired N,N-dimethylaminoethyl heptanoate is 51% based upon 1-nitro-2-octanone.

EXAMPLE II

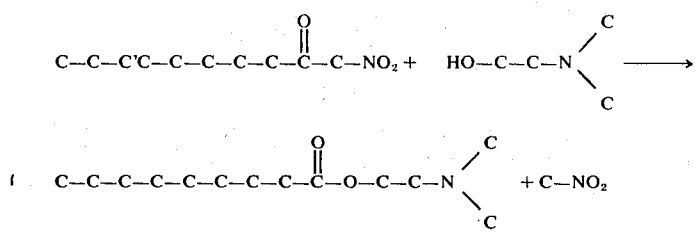

In accordance with practice of the process of this invention, ten parts of 1-nitro-2-decanone, 5.0 parts of dimethylaminoethanol, and 110 parts of dry benzene are admitted to a reaction vessel wherein they are refluxed for four hours. At the end of this time, there are distilled off from the reaction mixture 44 parts by weight of benzene solvent and 2.0 parts by weight of nitromethane. The remaining benzene is then distilled at atmospheric pressure and 80°C. Thereafter the residual dark oil is distilled at 106°–110°C, at 2mm Hg to yield 8.2 parts by weight of N,N-dimethylaminoethyl nonanoate, a pale yellow liquid having a boiling point of 106°–110°C/2mm and a refractive index $N_D^{24}$ 1.4355. (Yield 72%)

Results comparable to those obtained in Examples I and II may be obtained by reacting the following nitroketones and aminoalcohols:

| Example | Nitroketone | Aminoalcohol |
| --- | --- | --- |
| III | 1-nitro-2-butanone | dimethylamino ethanol |
| IV | 3-nitro-2-butanone | 1-dimethylamino-2-propanol |
| V | 1-nitro-2-pentanone | 2-dioctylamino-1-hexanol |
| VI | 3-nitro-2-pentanone | dicyclohexylamino ethanol |
| VII | 1-nitro-2-octanone | diethylamino ethanol |
| VIII | 1-nitro-2-decanone | dibutylamino ethanol |

EXAMPLE IX

In this example which represents practice of the novel process of this invention, a charge polymer of ethylene-propylene-1,4-hexadiene having a molecular weight $\overline{M}_n$ of 4445, an ethylene content of 65.2 mole percent, a propylene content of 32 mole percent, and a hexadiene content of 2.8 mole percent is nitroketonized in two steps. In the first step, nitrooxidation is effected by dissolving 15.2 g of polymer in 384 ml of carbon tetrachloride, cooling to about 1°C, saturating with oxygen, and then passing through the solution a combined stream of oxygen (ca. 13.6 ml/min.) and $N_2O_4$ (ca. 1.7ml./min.). Conclusion of reaction is evidenced by development of a brown color, $N_2O_4$, in the vapor phase above the system, after 0.77ml (0.0125 moles) of $N_2O_4$ are reacted with the double bonds (one double bond per 1220 grams) in the charge terpolymer.

The intermediate nitro peroxynitrate so obtained is converted to the nitroketone by adding 48 ml dimethylformamide to the solution at ice-bath temperature. Heat of reaction increases the temperature to 4°C during the conversion. Product polymer is isolated by pouring into an excess of methanol to give a recovery of 90% of the theoretical. Infra-red analysis reveals presence of carbonyl and nitro- functions and the essential absence of nitro peroxynitrate functions. Nitrogen content is 0.86%. corresponding to one nitroketone group for each 1630 molecular weight units. Molecular weight $\overline{M}_n$ is 3890, corresponding to ca 2.4 nitrogen atoms per molecule. 1.55 parts of the so nitroketonized polymer. 1.8 parts of dimethylaminoethanol, and 44 parts of dry benzene are refluxed at 80°C for 53 hours. During this time, the nitroketonized polymer is converted to a polymer having, in place of the nitroketone pendant chains, side chains bearing the carbo- N,N-dimethylaminoethoxy group. The reaction is followed by periodically withdrawing from the reaction mass an aliquot portion which is subjected to semiquantitative infrared analysis. Analysis indicates that after 51 hours, 32% of the $NO_2$ groups are retained in the polymer i.e. 68% of the nitroalkyl groups of the polymer have been split off and replaced by the carbo-N-N-dimethylaminoethoxy group.

After 53 hours of reflux, the solvent benzene is distilled off and 1.46 parts of product are recovered. Although it may be possible to purify the residue, it is found that it can be used as hereinafter set forth without further purification.

The product of this example is tested for dispersancy in lubricating oil in accordance with the Bench Sludge Test hereinbefore set forth. It is found that the product (in concentration of 3 wt % of the finished lubricating oil) has dispersancy ratings of BSI of 0.8 and BSII of 0.8. Such ratings are considered to be indicative of good dispersancy. The rating of BSII of less than 1.8 is particularly believed to be promising. The control petroleum base oil, in which these dispersancy ratings were determined, yielded ratings of BSI-2.0 and BSII-2.0; accordingly it may be noted that the novel product of this invention permitted attainment of improved results with respect to dispersancy.

EXAMPLE X

In this example which represents practice of the novel process of this invention, 3.0 parts of the same nitroketonized terpolymer prepared in Example IX is added to a reaction vessel together with 8.9 parts of dimethylaminoethanol and 17.6 parts of benzene. The reaction mixture is substantially anhydrous. After refluxing for 24 hours at ca. 87°–89°C, half of the reaction mixture is removed; 0.17 parts of sodium stearate catalyst is added and refluxing is continued for an additional 24 hours. At this time, some phase separation occurs through loss of some of the benzene solvent. The solid which precipitates is separated by decantation and may be heated to remove volatiles including residual benzene and thereafter recovered.

The product thus may be recovered in three fractions
A. 1.62 parts of the first fraction recovered after 24 hours at reflux this being recovered from the withdrawn reaction mixture by precipitating in methanol;
B. second fraction which may be recovered in amount of 1.09 parts, this corresponding to the product separating from the reaction mass after 40 hours of reflux, which product may be isolated by filtration; and C. 0.074 parts of a third fraction product recovered from the remaining reaction mass after removal of product (b), this being recovered by precipitating in methanol.

Testing of sample A in the Bench Sludge Test indicated that this product, which has lost 76% of the nitro function during the reaction, showed good dispersancy in lubricating oil. Specifically, BSI rating is 1.0 and BSII rating is 0.5. In view of the superior BSII rating, this product clearly indicates that substantial improvement may be made comparable untreated oil may have a BSI rating of 2.0 and a BSII rating of 2.0. Sample B yields a BSI rating of 1.3 and a BSII rating of 1.5. Sample C yields a BSI rating of 1.6 and a BSII rating of 1.5. Thus it will be noted that Samples B and C show improvement over the base oil.

EXAMPLES XI–XII

In control Example XI, the viscosity and viscosity index of Solvent Neutral Oil 7 (HF) are determined. In experimental Example XII, 3 parts of the polymer product of Example IX are added to 97 parts of the SNO 7; (HF) base oil; and the viscosimetric properties of the oil are determined.

| Property | Example XI* | XII |
|---|---|---|
| Kin Vis (cs) | | |
| 100°F | 27.6 | 50.0 |
| 212°F | 4.75 | 7.70 |
| Viscosity Index | 100 | 131 |

*Control

From the above, it will be apparent that the viscosity and viscosity index of the control oil may be improved substantially. The viscosity index, for example may be improved by 31 points from 100 to 131.

Comparable improvements in viscosity, viscosity index, and dispersancy may be achieved by using the following additives in SNO 7 Oil (HF) in amount of 3 parts of additive and 97 parts of oil.

EXAMPLE XIII

Dimethylaminoethyl ester of a completely nitroketonized EPT — specifically the nitroketonized terpolymer of ethylene-propylene-1,4-hexadiene containing 65.2 mol % ethylene, 32 mole % propylene, and 2.8 mole % hexadiene, $\overline{M}_n$ of 4445 and containing 1 nitroketone group per 1220 molecular weight units.

EXAMPLE XIV 3-dibutylaminopropyl ester of a completely nitroketonized EPT — specifically the nitroketonized terpolymer of ethylene-propylene-1,4-hexadiene containing 65.2 mol % ethylene, 32 mole % propylene, and 2.8 mole % hexadiene, $\overline{M}_n$ of 4445 and containing 1 nitroketone group per 1220 molecular weight units.

EXAMPLE XV

Diethylaminoethyl ester of a completely nitroketonized EPT — specifically the nitroketonized terpolymer of ethylene-propylene-1,4-hexadiene containing 65.2 mol % ethylene, 32 mole % propylene, and 2.8 mole % hexadiene, $\overline{M}_n$ of 4445 and containing 1 nitroketone group per 1220 molecular weight units.

EXAMPLE XVI

Diemethylaminoethyl ester of a 2% (of the available unsaturation) nitroketonized 1,2-polybutadiene $\overline{M}_n$ of 6150.

EXAMPLE XVII

3-Dibutylaminopropyl ester of a 2% (of the available unsaturation) nitroketonized 1,2-polybutadiene $\overline{M}_n$ of 6150.

EXAMPLE XVIII

Dimethylaminoethyl ester of an 8% (of the available unsaturation) nitroketonized 1,2-polybutadiene $\overline{M}_n$ of 6150.

EXAMPLE XIX

3-Dibutylaminopropyl ester of an 8% (of the available unsaturation) nitroketonized 1,2-polybutadiene $\overline{M}_n$ of 6150.

Although this invention has been illustrated by reference to specific embodiments, it will be apparent to those skilled in the art that various changes and modifications may be made which clearly fall within the scope of this invention.

We claim:
1. The method which comprises reacting (i) a nitroketonized polymer bearing pendant alpha nitroketone groups with (ii) a tertiary amino alcohol thereby forming a polymer bearing pendant aminoester groups; and recovering said polymer bearing said pendant aminoester groups.

2. The method as claimed in claim 1 wherein said nitroketonized polymer has a carbon-carbon backbone chain.

3. The method as claimed in claim 1 wherein said nitroketonized polymer is a nitroketonized EPT terpolymer having a molecular weight $\overline{M}_n$ of 300–100,000.

4. The method of preparing an aminoester as claimed in claim 1 wherein said alpha-nitroketone is a nitroketonized EPT terpolymer of ethylene, propylene, and 1,4-hexadiene.

5. The method of preparing a polymer bearing pendant aminoester groups.

$$R-\overset{O}{\underset{\|}{C}}-O-R''-N\overset{R'''}{\underset{R^{iv}}{\diagdown}}$$

which comprises reacting a nitroketone $$R-\overset{O}{\underset{\|}{C}}-\overset{H}{\underset{R'}{\overset{|}{C}}}-NO_2$$

with a tertiary amino alcohol $$HOR''-N\overset{R'''}{\underset{R^{iv}}{\diagdown}}$$

wherein R is a polymer-derived moiety, R''' and $R^{iv}$ are saturated hydrocarbon, R' is hydrogen or saturated hydrocarbon, and R'' is divalent saturated hydrocarbon, thereby forming product aminoester; and recovering said aminoester.

6. The method as claimed in claim 5 wherein R''' and R$^{iv}$ are $C_1$–$C_{30}$ saturated alkyl.

7. The method as claimed in claim 5 wherein R''' and R$^{iv}$ are $C_1$–$C_{10}$ saturated alkyl.

8. The method as claimed in claim 5 wherein R'' is ethylene — $CH_2$—$CH_2$—.

9. The method as claimed in claim 5 wherein said tertiary amino alcohol is a dimethylamino alcohol.

10. The method as claimed in claim 5 wherein said tertiary amino alcohol is dimethylamino ethanol.

11. The method as claimed in claim 5 wherein said polymer is an EPT polymer.

12. The method of preparing an aminoester as claimed in claim 5 wherein said alpha-nitroketone is a nitroketonized EPT terpolymer having a molecular weight $\overline{M}_n$ of 300–100,000.

13. A new aminoester polymer

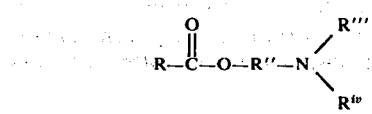

wherein R is a polymer moiety, R''' and R$^{iv}$ are monovalent saturated hydrocarbon groups, and R is divalent saturated hydrocarbon, said polymer having been prepared by the method which comprises reacting (i) a nitroketonized polymer bearing pendent alpha nitroketone groups with (ii) a tertiary amino alcohol.

14. The product of claim 13 wherein R''' and R$^{iv}$ are lower alkyl.

15. The product of claim 13 wherein R'' is ethylene —$CH_2$ — $CH_2$ —.

16. The product of claim 13 wherein R is an EPT derived hydrocarbon moiety.

17. A novel polymer having a carbon-carbon backbone chain and pendant therefrom a plurality of groups

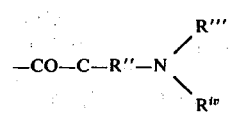

wherein R''' and R$^{iv}$ are saturated monovalent hydrocarbon, and R'' is divalent hydrocarbon, said polymer having a molecular weight $\overline{M}_n$ of 300–100,000 and containing one of said groups per 300–100,000 molecular weight units in said polymer, said polymer having been prepared by the method which comprises reacting (i) a nitroketonized polymer bearing pendent alpha nitroketone groups with (ii) a tertiary amino alcohol.

* * * * *